(12) United States Patent
Bichsel et al.

(10) Patent No.: US 7,112,184 B2
(45) Date of Patent: Sep. 26, 2006

(54) DISPOSABLE VAGINAL CLEANING DEVICE

(76) Inventors: John Bichsel, 21 Sunset Bay Dr., Bellair, FL (US) 33756; Catherine Montgomery, 2400 1st St. #6, Indian Rocks Beach, FL (US) 33785

( * ) Notice: Subject to any disclaimer, the term of this patent is extended or adjusted under 35 U.S.C. 154(b) by 192 days.

(21) Appl. No.: 10/953,909

(22) Filed: Sep. 29, 2004

(65) Prior Publication Data

US 2006/0069341 A1    Mar. 30, 2006

Related U.S. Application Data

(63) Continuation-in-part of application No. 10/952,621, filed on Sep. 28, 2004.

(51) Int. Cl.
*A61M 35/00* (2006.01)
(52) U.S. Cl. ...................... 604/1; 604/385.01
(58) Field of Classification Search ................ 604/1–3, 604/327–330, 358, 385.01
See application file for complete search history.

(56) References Cited

U.S. PATENT DOCUMENTS

| | | | |
|---|---|---|---|
| 3,228,398 A * | 1/1966 | Leonard et al. | ................. 604/1 |
| 3,724,463 A | 4/1973 | Vail | |
| 4,772,274 A | 9/1988 | Lukacs | |
| 5,045,058 A | 9/1991 | Demetrakopoulos | |
| 5,273,521 A * | 12/1993 | Peiler et al. | ................. 604/13 |
| 5,401,240 A | 3/1995 | Yang | |
| 5,542,914 A | 8/1996 | Van Iten | |
| 5,632,756 A * | 5/1997 | Kruglick | ..................... 606/162 |
| 2005/0026759 A1 * | 2/2005 | McKay et al. | ................. 492/56 |

* cited by examiner

*Primary Examiner*—Michele Kidwell
(74) *Attorney, Agent, or Firm*—Melvin K. Silverman; Yi Li

(57) ABSTRACT

A vaginal cleaning device includes an elongated applicator including an axial support post having a front end and a rear end, a head connected to the front end, a circular disk with a plurality of apertures disposed at the rear end; and a flexible absorbent material disposed around the axial support post between the head and the circular disk. The device has an elongated handle connected to the elongated applicator, a hollow outer tube with a front portion disposed around the elongated applicator and a rear portion disposed telescopically outside a hollow inner tube. The hollow inner tube has the front open end disposed against the rear side of the circular disk of the elongated applicator and a rear portion disposed around the elongated handle. Also disclosed is a method of using the vaginal cleaning device.

20 Claims, 4 Drawing Sheets

DISPOSABLE VAGINAL CLEANING DEVICE

CROSS REFERENCE TO RELATED APPLICATION

This application is a continuation-in-part of patent application Ser. No. 10/952,621, filed on Sep. 28, 2004, which is herein incorporated by reference in its entirety.

FIELD OF THE INVENTION

The invention pertains to vaginal cleaning and hygiene device.

BACKGROUND OF THE INVENTION

The vagina is a relatively long hollow, tube like structure that extends from the cervix at the outer end of the uterus down to the labia minora. The interior of the vagina is composed of a mucous membrane and an outer, smooth muscle closely attached to it. While glands are present in the vaginal lining itself, vaginal secretions can arise from the glands in the cervical canal of the uterus such as Bartholin's and Skene's glands. Normally such secretions are clean, but occasionally debris in the form of blood or deposition of seminal fluid can accumulate. Accordingly, it is desirable at times to be able to have a convenient disposable applicator to clean and refresh the vaginal canal to add to or treat the vaginal canal with medications, germicides, or deodorants.

U.S. Pat. No. 5,045,058 by Demetrakopoulos cleanses the vagina by providing an apparatus that delivers lather to the vaginal canal. Vaginal cleaning devices have been addressed in the prior art in terms of a swabbing applicator, as may be seen in U.S. Pat. No. 3,724,463 to Vail. Also, other vaginal cleaning devices that have been addressed in the prior art include a syringe apparatus as may be seen in U.S. Patent No. 4,772,274 to Lukacs and U.S. Pat. No. 5,401,240 to Yang. U.S. Pat. No. 5,542,914 to Van Iten is an encapsulated tampon with applicator using a similar means of insertion into the vaginal canal. However, these devices do not satisfactorily consider all issues of size, convenience, portability, simplicity of construction, and effectiveness that are addressed herein.

SUMMARY

In one embodiment, the present invention directed to a vaginal cleaning device, which comprises an elongated applicator, an elongated handle, a hollow inner tube and a hollow outer tube. The elongated applicator comprises an axial support post having a front end and a rear end; a head with a rear surface connected to the front end of the axial support post; and a circular disk disposed at the rear end of the axial support post; and a flexible absorbent material disposed around the axial support post between the head and the circular disk; wherein the circular disk has a plurality of apertures. The elongated handle has a front end connected to a rear side of the circular disk of the applicator. The hollow inner tube has a first front open end and a first rear open end; the hollow inner tube being disposed around the handle with the first front open end against the rear side of the circular disk of the elongated applicator. The hollow outer tube having a second front open end and a second rear open end; wherein a rear portion of the hollow outer tube is disposed telescopically outside the hollow inner tube, and a front portion of the hollow outer tube is disposed around the elongated applicator with the second front open end around the head. The inner diameter of the hollow outer tube is substantially same as outer diameters of the head and the circular disk.

In an alternative embodiment, the hollow outer tube has a front end having a structure of multiple petal closure structure encapsulating the head of the elongated applicator.

In a further embodiment, the present invention is directed to a method of using the vagina cleaning device of the present invention. The method includes the steps of providing a vagina cleaning device as described above; adding fluid through the first rear open end into the hollow inner tube, and allowing the fluid to enter into the applicator to wet the flexible absorbent material; inserting the front portion of the hollow outer tube of the vaginal cleaning device into the vagina of a user; pushing the first rear open end of the hollow inner tube forward while holding the hollow outer tube to push the applicator out of the hollow outer tube into the vagina; removing the hollow inner tube and the hollow outer tube in a backward direction along the handle; moving the applicator inside the vagina using the handle to clean the vagina; and removing the applicator out from the vagina.

It is an object of the present invention to provide a vaginal cleaning device having functions of cleaning, deodorizing, and medicating the vaginal canal.

Another object is to provide a portable, efficient and effective means to cleanse the vaginal canal prior to or after sexual intercourse.

It is a yet further object to provide a vaginal cleaning device that is more effective than prior art solutions of lathering or scrubbing, and more convenient to use then syringe-like devices.

The above and yet other objects and advantages of the present invention become apparent from the hereinafter set forth Brief Description of the Drawings, Detailed Description of the Invention, and Claims appended herewith.

DETAILED DESCRIPTION OF THE INVENTION

Figure 1:
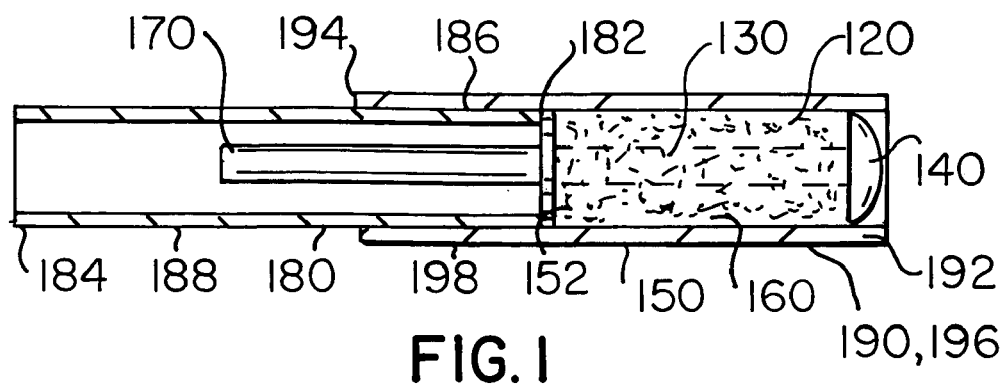
FIG. 1 is a cut-offside view of one embodiment of the vaginal cleaning device of the present invention.

In one embodiment, the present invention provides a vaginal cleaning device, as shown in FIGS. 1 thru 5. The vaginal cleaning device 100 comprises an elongated applicator 120, a hollow inner tube 180 and a hollow outer tube 190 and an elongated handle 170.

The elongated applicator 120 comprises an axial support post 130 a front end 132 and an opposing rear end 134 with a head 140 with a rear surface connected to the front end 132 and a circular disk 150 disposed around the rear end 134; and a flexible absorbent material 160 disposed around the axial support post 130 between the head 140 and the circular disk 150. The handle means 170 is connected to the rear end 134 of the axial support post 130. Preferably, the handle means 170 is an integrally dependent from the axial support post 130.

Figure 4:
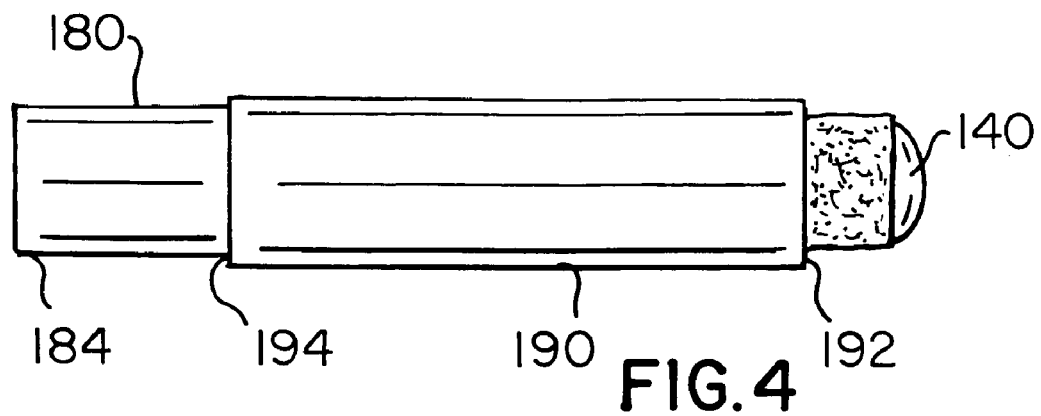
FIG. 4 is perspective view of the device in FIG. 1, showing a portion of the applicator being partially pushed out from the hollow outer tube.
Figure 8:
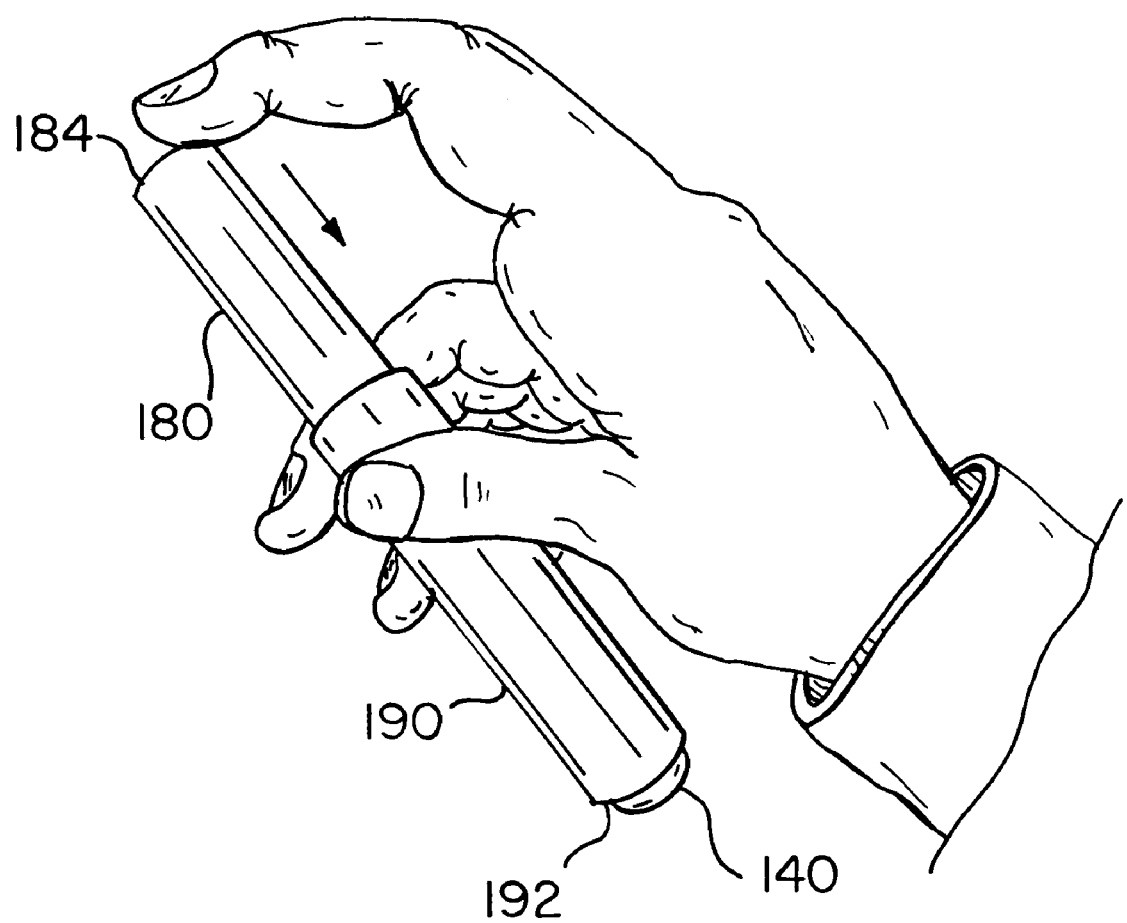
FIG. 8 is an illustrative view of showing the use of the vaginal cleaning device of FIG. 1.

As shown in FIG. 1, the elongated applicator 120 is housed within a hollow outer tube 190. The hollow outer tube 190 has a front open end 192 and a rear open end 194, a front portion 196 disposed around the elongated applicator 120 with the front open end 192 and the head 140, and a rear portion 198 telescopically outside a front portion 186 of the hollow inner tube 180. The hollow inner tube 180 has a front open end 182 disposed against the rear side 152 of the circular disk 150, a rear open end 184, and a rear portion 188 disposed around the elongated handle 170. When a force is applied on to the rear open end 184 while holding the hollow outer tube 190, as illustrated in FIG. 8, the elongated applicator 120 is pushed out from the hollow outer tube 190, as shown in FIG. 4.

Figure 3:
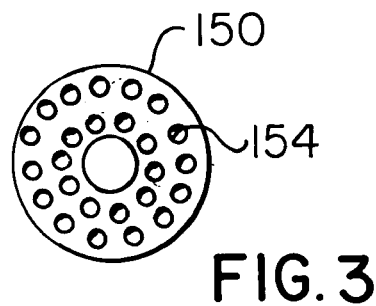
FIG. 3 is an enlarged bottom view of the circular disk shown in FIGS. 1 and 2.
Figure 5:
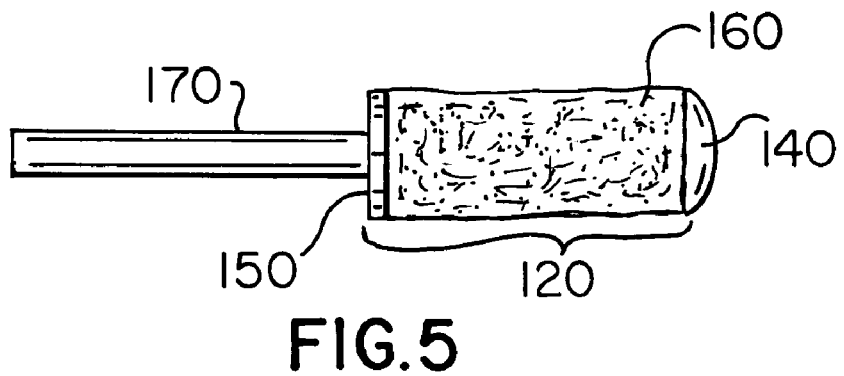
FIG. 5 is a perspective side view of a part of the vaginal cleaning device without the hollow inner or outer tubes.

The head 140 has a semi-spherical front surface for comfortable delivery of the elongated applicator 120 into the vagina of a user. The rear surface of the head 140 is substantially planar. As shown in FIGS. 3 and 5, the circular disk 150 has a plurality of apertures 154 for allowing a fluid from the rear side 152 of the circular disk 150 to enter into the flexible absorbent material 160. Preferably, the outer diameter of the head 140 is from about 3/8 to 5/8 inches, similar to an outer diameter of the current commercial product tampon. The outer diameter of the circular disk 150 is substantially same to that of the head 140. The head 140 and the circular disk 150 retain the flexible absorbent material 160 in position and prevent dislocation of the flexible absorbent material 160 during use.

The inner diameter of the hollow outer tube 190 is substantially the same to the outer diameters of the head 140, the circular disk 150, and the outer diameter of the hollow inner tube 180.

Figure 5A:
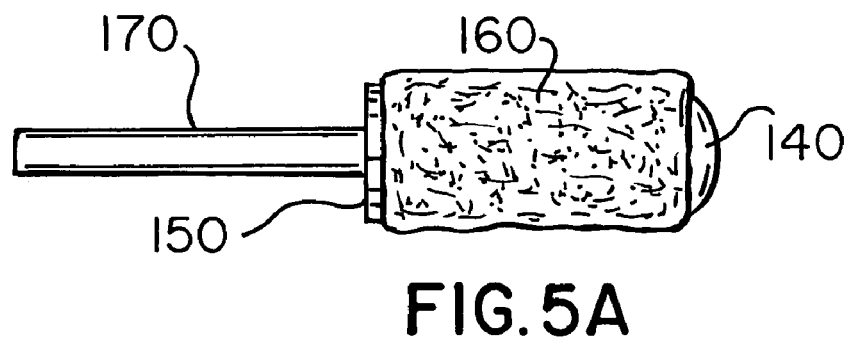
FIG. 5a is a perspective side view of the vaginal cleaning device of FIG. 5, wherein the flexible absorbent material is expandable upon being released from the hollow outer tube.

Preferably, the flexible absorbent material 160 is porous, such as a sponge material, or ribbed cotton. More preferably, an FDA approved material, such as a sponge made of hydrophilic polyurethane foam, is used. The porous surface of the sponge helps to gently scrub the interior of the vagina, and enhances the effectiveness of cleaning. In one embodiment, the flexible absorbent material 160 has a substantially same outer diameter as that of the head 140 and the circular disk 150, as shown in FIG. 5. Alternatively, the flexible absorbent material 160 can also be expandable, which expands in width upon being released from the hollow outer tube 190, as shown in FIG. 5A.

Figure 2:
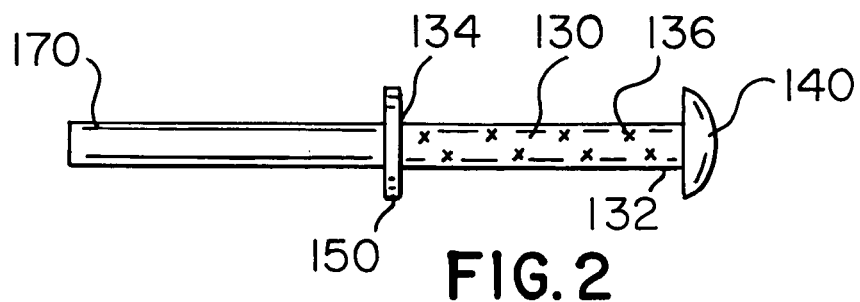
FIG. 2 is a perspective side view of a part of the vaginal cleaning device of FIG. 1, without the flexible absorbent material or the hollow inner and outer tubes.
Figure 2A:
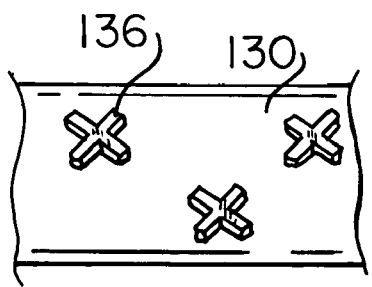
FIG. 2a is an enlarged view of the retention means of the axial support post of the device shown in FIG. 2.

In a preferred embodiment, the axial support post 130 further comprises retention means 136. As shown in FIGS. 2 and 2a, the retention means 136 are a plurality of protruding short rims arranged in a shape of a cross. However, it should be understood that other shapes and geometries can also be used for the retention means. The retention means 136 are disposed around the surface of the axial support post 130, which further assists to hold the flexible absorbent material 160 in place during use.

The axial support post, head and retention means can be made of a low density polyethylene, preferably, FDA approved material such as USP Class 6B1-ISO10993. Moreover, the axial support post, head, and retention means can also be made of other FDA approved moldable plastic materials. The hollow inner and outer tubes are preferably made of the same low density polyethylene material. The tubes may also be made of a cardboard or other paper product, preferably lined with a water resistant material to prevent deformation of the tube once fluid has been inserted.

Additionally, the vaginal cleaning device 100 can further comprise a pharmaceutically acceptable cleaning agent in the flexible absorbent material 160. The cleaning agent located in the flexible absorbent material 160 can be moistened with fluid before insertion. The cleaning agent further assists the cleaning.

Figure 6:
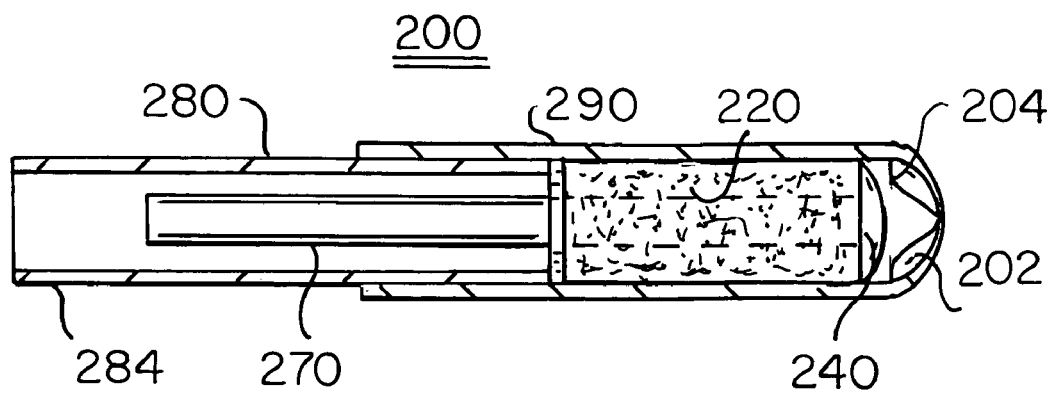
FIG. 6 is a cut-off view of the vaginal cleaning device of a further embodiment of the present invention.
Figure 7:
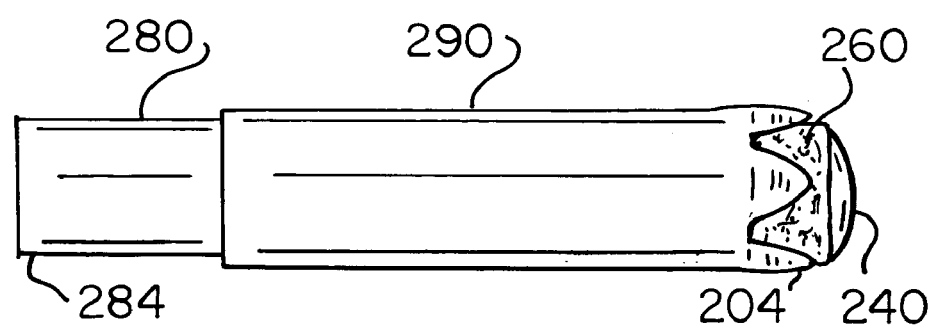
FIG. 7 is a perspective side view of the vaginal cleaning device of FIG. 6, showing a portion of the applicator being partially pushed out from the hollow outer tube.

In a further embodiment, the present invention provides a vaginal cleaning device 200 as shown in FIGS. 6–7. Similarly, the vaginal cleaning device 200 comprises an elongated applicator 220, a hollow inner tube 280 and a hollow outer tube 290 and a handle 270. The structure, materials, and functionality of the elongated applicator 220, elongated handle 270 and hollow inner tube 280 are the same as those of the elongated applicator 120, elongated handle 170, and hollow inner tube 180 described previously.

Different from the vagina cleaning device 100, the hollow outer tube 290 has a front end 202 which has a multiple petal closure structure as shown in FIGS. 6 and 7. Preferably, the multiple petal closure structure has five petals 204 in a form of "five petal closure structure" currently used in outer shell of the commercial product of tampon. The method of making the multiple petal closure structure is known in the art.

The front end having a multiple petal closure structure 202 of the hollow outer tube can be pushed open by the head 240 of the elongated applicator 220 when applying a force at the rear open end 284 of the hollow inner tube 280, thereby exposing the elongated applicator 220, as shown in FIG. 7. The multiple petal closure structure provides a smooth front surface for comfortably inserting the device into the vagina.

When in use, the user adds water or other suitable liquids through the rear open end 184 into the hollow inner tube 180, allowing the fluid to enter into the tube passing through the apertures 154 located on the circular disk 150 to wet the flexible absorbent material 160.

Since the vaginal cleaning device 100 or 200 has an inner diameter of the hollow outer tube 190 substantially the same as the outer diameters of the head 140 and the circular disk 150, the fluid is maintained inside the elongated applicator 120 prior to inserting the cleaning device.

The user inserts the front portion 196 of the hollow outer tube 190 of the vaginal cleaning device 100. The user then pushes the rear open end 184 of the hollow inner tube 180 forward while holding the hollow outer tube 190 to push the elongated applicator 120 out of the hollow outer tube 190 into the vagina.

The hollow inner tube 180 and the hollow outer tube 190 are then removed in a backward direction along the elongate handle 170. The user can move the elongated applicator 120 inside the vagina using the elongate handle 170 to clean the vagina. By moving the elongated applicator 120 the user can rotate the applicator, move forward and backward along the vagina, or combination of both. The user then removes the elongated applicator 120 out from the vagina.

Although the method of using the vaginal cleaning device of the present invention is described above with the vaginal cleaning device 100, the same process is also used with the vaginal cleaning device 200.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

We claim:

1. A vaginal cleaning device, comprising:
   (a) an elongated applicator comprising an axial support post having a front end and a rear end; a head with a rear surface connected to said front end of said axial support post; and a circular disk disposed around said rear end of said axial support post; and a flexible absorbent material disposed around said axial support post between said head and said circular disk; wherein said circular disk has a plurality of apertures;
   (b) an elongated handle having a front end connected to said rear end of said elongated applicator;
   (c) a hollow inner tube having a first front open end and a first rear open end; said hollow inner tube being disposed around said handle with said first front open end against said rear side of said circular disk of said elongated applicator; and
   (d) a hollow outer tube having a second front open end and a second rear open end; wherein a rear portion of said hollow outer tube is disposed telescopically outside said hollow inner tube, and a front portion of said hollow outer tube is disposed around said elongated applicator with said second front open end around said head.

2. The vaginal cleaning device as recited in claim 1, wherein an inner diameter of said hollow outer tube is substantially same as outer diameters of said head and said circular disk.

3. The vaginal cleaning device as recited in claim 1, wherein said axial support post has retention means on an external surface thereof, for retaining said flexible absorbent material in position.

4. The vaginal cleaning device as recited in claim 3, wherein said retention means is a plurality of protruding rims positioned around said axial support post.

5. The vaginal cleaning device as recited in claim 1, wherein said flexible absorbent material is a sponge made of hydrophilic polyurethane foam.

6. The vaginal cleaning device as recited in claim 1, wherein said flexible absorbent material is ribbed cotton.

7. The vaginal cleaning device as recited in claim 1, wherein said flexible absorbent material is expandable upon releasing from said hollow outer tube.

8. The vaginal cleaning device as recited in claim 1 further comprising a pharmaceutically acceptable cleaning agent in said flexible absorbent material.

9. A vaginal cleaning device, comprising:
   (a) an elongated applicator comprising an axial support post having a front end and a rear end; a head with a rear surface connected to said front end of said axial support post; and a circular disk disposed at said rear end of said axial support post; and a flexible absorbent material disposed around said axial support post between said head and said circular disk; wherein said circular disk has a plurality of apertures;
   (b) an elongated handle having a front end connected to a rear side of said circular disk of said applicator;
   (c) a hollow inner tube having a first front open end and a first rear open end; said hollow inner tube being disposed around said handle with said first front open end against said rear side of said circular disk of said applicator; and
   (d) a hollow outer tube having a front end and a second rear open end; said front end thereof having a multiple petal closure structure; wherein a rear portion of said hollow outer tube is disposed telescopically outside said hollow inner tube, and a front portion of said hollow outer tube is disposed around said applicator with said front end thereof encapsulating said head.

10. The vaginal cleaning device as recited in claim 9, wherein said front end of said hollow outer tube can be pushed open by said head of said elongated applicator when applying a force at said first rear open end of said hollow inner tube, thereby exposing said elongated applicator.

11. The vaginal cleaning device as recited in claim 9, wherein an inner diameter of said hollow outer tube is substantially same as outer diameters of said head and said circular disk.

12. The vaginal cleaning device as recited in claim 9, wherein said axial support post has retention means on an external surface thereof, for retaining said flexible absorbent material in position.

13. The vaginal cleaning device as recited in claim 12, wherein said retention means is a plurality of protruding rims positioned around said axial support post.

14. The vaginal cleaning device as recited in claim 9, wherein said flexible absorbent material is a sponge made of hydrophilic polyurethane foam.

15. The vaginal cleaning device as recited in claim 9, wherein said flexible absorbent material is ribbed cotton.

16. The vaginal cleaning device as recited in claim 9, wherein said flexible absorbent material is expandable upon releasing from said hollow outer tube.

17. The vaginal cleaning device as recited in claim 9 further comprising a pharmaceutically acceptable cleaning agent in said flexible absorbent material.

18. A method of cleaning vagina comprising the steps of:
   (a) providing a cleaning device which comprises:
   (i) an elongated applicator comprising an axial support post having a front end and a rear end; a head with a rear surface connected to said front end of said axial support post; and a circular disk disposed at said rear end of said axial support post; and a flexible absorbent material disposed around said axial support post between said head and said circular disk; wherein said circular disk has a plurality of apertures;
   (ii) an elongated handle having a front end connected to a rear side of said circular disk of said applicator;
   (iii) a hollow inner tube having a first front open end and a first rear open end; said hollow inner tube being disposed around said handle with said first front open end against said rear side of said circular disk of said applicator; and
   (iv) a hollow outer tube having a second front open end and a second rear open end; wherein a rear portion of said hollow outer tube is disposed telescopically outside said hollow inner tube, and a front portion of said hollow outer tube is disposed around said applicator with said second front open end around said head;
(b) adding fluid through said first rear open end into said hollow inner tube, and allowing said fluid to enter into said applicator to wet said flexible absorbent material;
(c) inserting said front portion of said hollow outer tube of said vaginal cleaning device into the vagina of a user;
(d) pushing said first rear open end of said hollow inner tube forward while holding said hollow outer tube to push said applicator out of said hollow outer tube into the vagina;
(e) removing said hollow inner tube and said hollow outer tube in a backward direction along said handle;
(f) moving said applicator inside the vagina using said handle to clean the vagina; and
(g) removing said applicator out from the vagina.

19. The method of cleaning vagina as recited in claim 18, wherein said cleaning device has an inner diameter of said hollow outer tube substantially same as outer diameters of said head and said circular disk to retain fluid inside said applicator prior to inserting said cleaning device.

20. The method of cleaning vagina as recited in claim 18, wherein said moving said applicator in step (f) includes rotating said applicator, moving forward and backward along the vagina, or combination thereof.

* * * * *